(12) United States Patent
Miller et al.

(10) Patent No.: US 7,938,858 B2
(45) Date of Patent: May 10, 2011

(54) SPINAL IMPLANT SYSTEM

(75) Inventors: David F. Miller, Cordova, TN (US); Marc M. Peterman, Memphis, TN (US); Lukas G. Eisermann, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 182 days.

(21) Appl. No.: 11/097,553

(22) Filed: Apr. 1, 2005

(65) Prior Publication Data
US 2005/0228501 A1   Oct. 13, 2005

Related U.S. Application Data

(63) Continuation-in-part of application No. 10/662,928, filed on Sep. 15, 2003.

(51) Int. Cl.
*A61F 2/44* (2006.01)
(52) U.S. Cl. .................. 623/17.14; 623/17.11; 606/266
(58) Field of Classification Search .... 623/17.11–17.16; 606/246–249, 254–259, 53, 60, 245, 90, 606/99
See application file for complete search history.

(56) References Cited

U.S. PATENT DOCUMENTS

| | | | | |
|---|---|---|---|---|
| 3,426,364 A | * | 2/1969 | Lumb | 623/17.15 |
| 4,401,112 A | * | 8/1983 | Rezaian | 606/279 |
| 4,554,914 A | | 11/1985 | Kapp et al. | |
| 4,892,545 A | | 1/1990 | Day et al. | |
| 4,932,975 A | | 6/1990 | Main et al. | |
| 5,084,049 A | * | 1/1992 | Asher et al. | 606/61 |
| 5,236,460 A | | 8/1993 | Barber | |
| 5,246,458 A | * | 9/1993 | Graham | 623/17.14 |
| 5,258,031 A | | 11/1993 | Salib et al. | |
| 5,360,430 A | * | 11/1994 | Lin | 606/61 |
| 5,401,269 A | | 3/1995 | Buttner-Janz et al. | |
| 5,423,816 A | | 6/1995 | Lin | |
| 5,443,515 A | | 8/1995 | Cohen et al. | |
| 5,458,641 A | | 10/1995 | Ramirez Jimenez | |
| 5,474,555 A | * | 12/1995 | Puno et al. | 606/266 |
| 5,480,442 A | | 1/1996 | Bertagnoli | |
| 5,534,029 A | * | 7/1996 | Shima | 623/17.15 |
| 5,556,431 A | | 9/1996 | Buttner-Janz | |
| 5,562,738 A | | 10/1996 | Boyd et al. | |
| 5,674,294 A | | 10/1997 | Bainville et al. | |
| 5,674,296 A | | 10/1997 | Bryan et al. | |
| 5,693,099 A | * | 12/1997 | Harle | 623/23.19 |
| 5,702,453 A | * | 12/1997 | Rabbe et al. | 623/17.16 |

(Continued)

FOREIGN PATENT DOCUMENTS
DE   9107494.0   9/1991
(Continued)

OTHER PUBLICATIONS

Dhandapani KM, Brann DW., Transforming Growth Factor-Beta: a Neuroprotective Factor in Cerebral Ischemia. 2003, 2 pages.

(Continued)

*Primary Examiner* — Eduardo C Robert
*Assistant Examiner* — Lynnsy Schneider

(57) ABSTRACT

Embodiments of the invention include devices and methods for performing a corpectomy or spinal disc replacement. Devices may include an inferior bearing that is implantable in an inferior vertebral body and a superior bearing that is implantable in a superior vertebral body. The bearings of some embodiments have a support member rotatably coupled between the bearings, and a fixation device may attach the vertebral bodies to the support member with a fastener.

34 Claims, 5 Drawing Sheets

U.S. PATENT DOCUMENTS

| | | | |
|---|---|---|---|
| 5,888,226 A | 3/1999 | Rogozinski | |
| 5,893,889 A | 4/1999 | Harrington | |
| 5,895,428 A * | 4/1999 | Berry | 623/17.15 |
| 5,899,941 A | 5/1999 | Nishijima et al. | |
| 5,916,267 A | 6/1999 | Tienboon | |
| 6,001,130 A | 12/1999 | Bryan et al. | |
| 6,063,121 A * | 5/2000 | Xavier et al. | 623/17.15 |
| 6,106,557 A * | 8/2000 | Robioneck et al. | 623/17.15 |
| 6,156,067 A | 12/2000 | Bryan et al. | |
| 6,159,211 A * | 12/2000 | Boriani et al. | 606/279 |
| 6,190,413 B1 | 2/2001 | Sutcliffe | |
| 6,299,644 B1 | 10/2001 | Vanderschot | |
| 6,375,682 B1 | 4/2002 | Fleischmann et al. | |
| 6,375,683 B1 | 4/2002 | Crozet et al. | |
| 6,395,030 B1 | 5/2002 | Songer et al. | |
| 6,540,785 B1 | 4/2003 | Gill et al. | |
| 2002/0077702 A1 | 6/2002 | Castro | |
| 2002/0169508 A1 | 11/2002 | Songer et al. | |
| 2003/0135277 A1 | 7/2003 | Bryan et al. | |
| 2004/0176843 A1 | 9/2004 | Zubok et al. | |
| 2005/0060034 A1 | 3/2005 | Berry et al. | |
| 2005/0085914 A1* | 4/2005 | Lange et al. | 623/17.11 |
| 2005/0090898 A1* | 4/2005 | Berry et al. | 623/17.11 |
| 2005/0256578 A1* | 11/2005 | Blatt et al. | 623/17.15 |
| 2006/0074490 A1* | 4/2006 | Sweeney | 623/17.15 |

FOREIGN PATENT DOCUMENTS

| | | |
|---|---|---|
| EP | 0567424 | 1/1998 |
| EP | 0974319 | 10/2001 |
| EP | 1188424 | 3/2002 |
| EP | 1212992 | 6/2002 |
| EP | 0978258 | 10/2002 |
| GB | 2290716 | 1/1996 |
| WO | WO 98/44878 | 10/1998 |
| WO | WO 98/49975 | 11/1998 |
| WO | WO 99/65412 | 12/1999 |
| WO | WO 01/97744 | 12/2001 |

OTHER PUBLICATIONS

U.S. Appl. No. 60/446,963, filed Feb. 12, 2003, Eisermann et al.
U.S. Appl. No. 10/423,712, filed Apr. 25, 2003, Shipp, et al.
U.S. Appl. No. 10/752,724, filed Jan. 7, 2004, Eisermann.
U.S. Appl. No. 10/752,725, filed Jan. 7, 2004, Eisermann.
U.S. Appl. No. 10/752,860, filed Jan. 7, 2004, Eisermann.
U.S. Appl. No. 10/773,494, filed Feb. 6, 2004, Eisermann et al.
U.S. Appl. No. 10/773,814, filed Feb. 6, 2004, Eisermann et al.
U.S. Appl. No. 10/773,815, filed Feb. 6, 2004, Eisermann et al.
U.S. Appl. No. 10/774,078, filed Feb. 6, 2004, Eisermann et al.
U.S. Appl. No. 10/774,135, filed Feb. 6, 2004, Eisermann et al.
U.S. Appl. No. 10/774,157, filed Feb. 6, 2004, Eisermann et al.

* cited by examiner

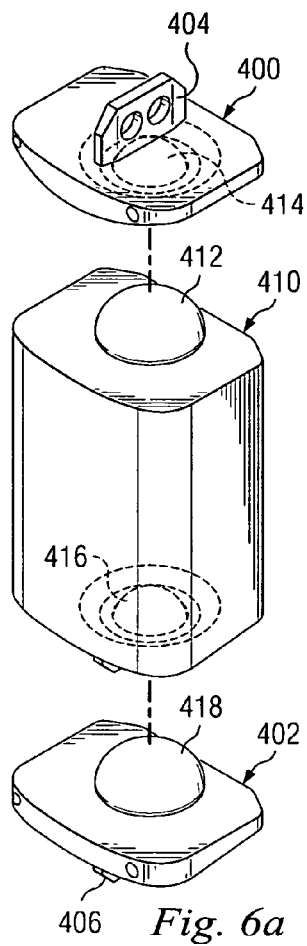
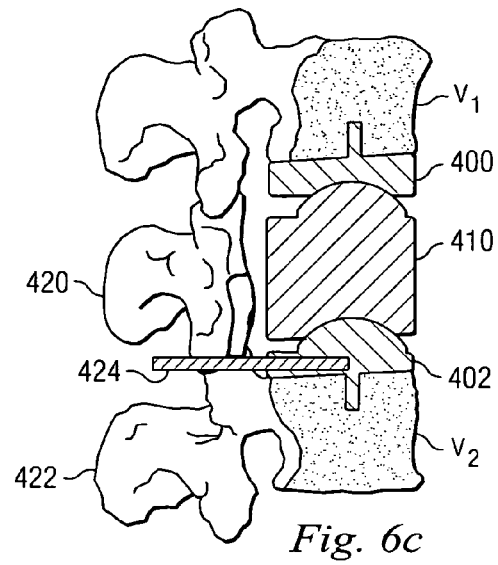
Fig. 6c
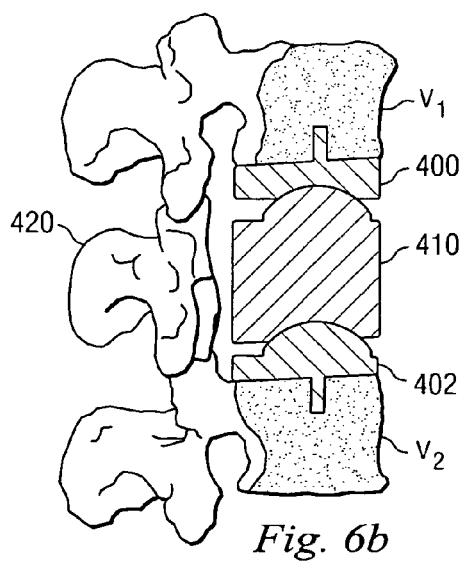
Fig. 6a
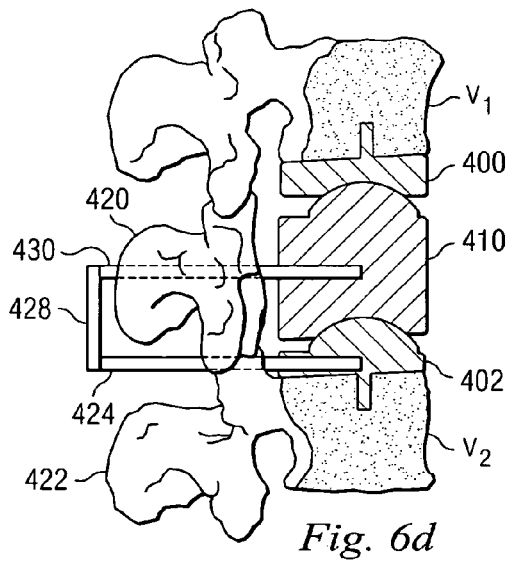
Fig. 6d
Fig. 6b

SPINAL IMPLANT SYSTEM

CROSS-REFERENCE TO RELATED APPLICATIONS

This application is a continuation-in-part of U.S. patent application Ser. No. 10/662,928, entitled "REVISABLE PROSTHETIC DEVICE," filed Sep. 15, 2003, which is hereby incorporated by reference in its entirety.

FIELD OF THE INVENTION

The present invention relates generally to the field of spinal implants, and more particularly relates to corpectomy and disc replacement devices and methods for the replacement of one or more vertebral bodies or discs.

BACKGROUND

A corpectomy is the excision of one or more vertebral bodies, usually combined with replacement of the removed body or bodies with a prosthesis or bone graft. A corpectomy may be necessary to correct a degenerative condition, to treat a traumatic injury, to replace vertebral bodies damaged by tumors or other diseases, or in other situations as deemed appropriate by a physician.

Implants and methods useful in performing corpectomy procedures have been known in the art for a number of years. Many of the previous implants and methods sought to create fixed constructs designed to eliminate relative movement between the vertebrae to which the implants were attached. Fixed constructs have been used with some success. However, it is difficult to achieve a securely fixed construct with a corpectomy device because the distance between the fixed vertebrae is relatively large. Consequently, in practice, some amount of motion typically occurs at the interface of the corpectomy device and the vertebrae. The motion may be very small—sometimes called "micro-motion." Nonetheless, even micro-motion applied through a large number of cycles can cause loosening of an implant. Loosening may necessitate corrective surgery with its associated cost, pain, and inconvenience.

Fixed constructs may also be limited because they fail to provide interfaces with the vertebrae that easily adapt to physiologically unusual, deformed, diseased, or damaged vertebral body surfaces. It is common practice to chisel or machine away portions of a vertebra to make the vertebra conform to an implant. This may cause additional surgical time and expense, and trauma to a patient.

Some of the prior implants and methods provided ball-in-socket or hinged connections rather than fixed constructs. Such flexible joints can be problematic because they may not provide an adequately stable construct to support a patient's weight and activities, especially where the patient has experienced soft tissue damage or degeneration at or near the corpectomy site.

The description herein of certain disadvantages and problems associated with known devices, apparatus, and methods is not intended to limit the scope of the invention to the exclusion of those known devices, apparatus, and methods. Indeed, embodiments of the invention may include some or all of the known devices, apparatus, and methods without suffering from the disadvantages and problems described herein.

SUMMARY

Embodiments of an improved device and method may provide stable but motion tolerant fixation. Improved devices and methods may also be adaptable to the geometry of the vertebrae, including irregular vertebrae, with less or no removal of vertebral tissue. An improved device in some embodiments would have components that, in addition to use in a corpectomy construct, are components of a disc replacement device.

An embodiment of the invention is an implantable corpectomy device having an inferior bearing coupled with an inferior vertebral body. A support member is slidably engaged with the inferior bearing, and the support member is configured to transfer load along its longitudinal axis and into the inferior bearing. A superior bearing is coupled with a superior vertebral body that is slidably engaged with the support member. The support member is configured to transfer load along its longitudinal axis and into the superior bearing. A fixation device is configured to couple with at least one of the inferior vertebral body and the superior vertebral body through a first bone fixation element at one end of the fixation device. The fixation device is configured to couple with the support member.

An additional embodiment of the invention includes a spinal implant system having an inferior bearing means for bearing against an inferior vertebral body, and a superior bearing means for bearing against a superior vertebral body. The spinal implant system optionally includes a support means for providing support between the inferior bearing means and superior bearing means, and optionally a fixation means for coupling the inferior and superior vertebral bodies to the support means.

Another embodiment of the invention is a spinal implant system having an inferior bearing coupled with an inferior vertebral body and a support member configured to slidably engage with the inferior bearing through a first joint. The system also has a superior bearing coupled with a superior vertebral body. The superior bearing is configured to slidably engage with the support member through a second joint. The inferior bearing and the superior bearing are configured to slidably engage with each other.

An embodiment of the invention is an implantable corpectomy device with an inferior bearing coupled with an inferior vertebral body and a support member slidably engaged with the inferior bearing. The support member may be configured to transfer load along its longitudinal axis and into the inferior bearing. The implantable corpectomy device may also include a superior bearing coupled with a superior vertebral body and slidably engaged with the support member. The support member may be configured to transfer load along its longitudinal axis and into the superior bearing. The implantable corpectomy device may also have a fixation device configured to couple with at least one of the inferior vertebral body and the superior vertebral body through a first bone fixation element at one end of the fixation device, and the fixation device configured to couple with the support member.

Yet another embodiment of the invention is a method of implanting a corpectomy device that includes implanting an inferior bearing into an inferior vertebra and implanting a superior bearing into a superior vertebra. Embodiments of the method may include placing a support member between the inferior bearing and the superior bearing such that the support member is rotatably coupled to the inferior bearing and rotatably coupled to the superior bearing, coupling a fixation device to at least one of the inferior vertebra and the superior vertebra with a first bone fixation element, and coupling the fixation device to the support member with a fastener.

Still another embodiment of the invention is a method of implanting a corpectomy device. The method includes coupling an inferior bearing with an inferior vertebra, coupling a superior bearing with a superior vertebra, and placing a support member between the inferior bearing and the superior bearing such that the support member is slidably engaged with the inferior bearing and slidably engaged with the superior bearing. The method also includes coupling a fixation device to at least one of the inferior vertebra and the superior vertebra with a first bone fixation element, and coupling the fixation device to the support member.

BRIEF DESCRIPTION OF THE DRAWINGS

FIG. 6a is an exploded view of a corpectomy device according to another embodiment of the present disclosure.

FIG. 6b is a lateral view depicting the corpectomy device of FIG. 6a disposed between a pair of vertebral bodies.

FIG. 6c is a lateral view of the corpectomy device of FIG. 6b connected to a pair of vertebral bodies.

FIG. 6d is a lateral view of the corpectomy device of FIG. 6b connected to a linkage system.

DETAILED DESCRIPTION

Figure 1:
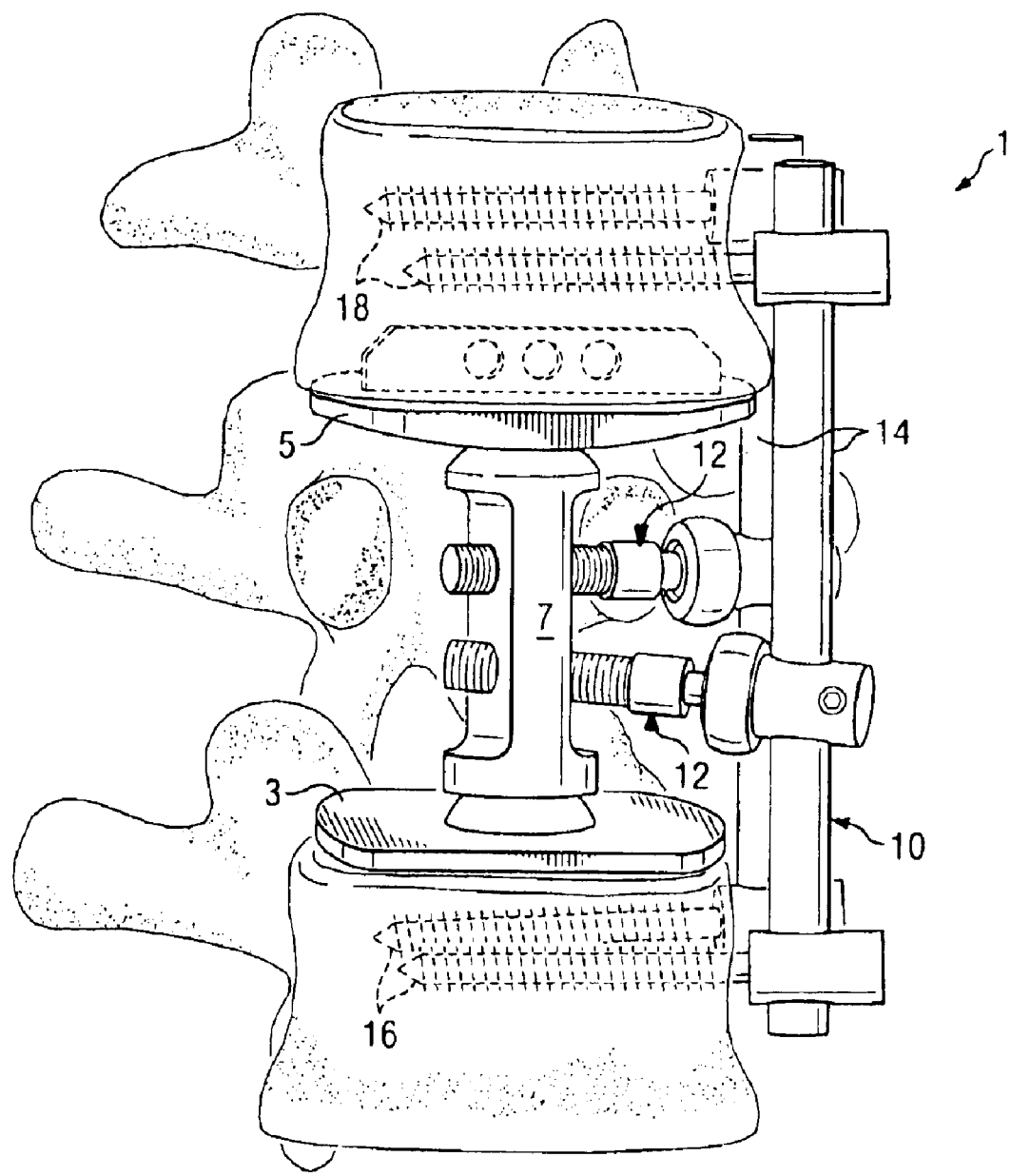
FIG. 1 is an isometric view of an embodiment of an implantable corpectomy device implanted between vertebrae of a spine.
Figure 5:
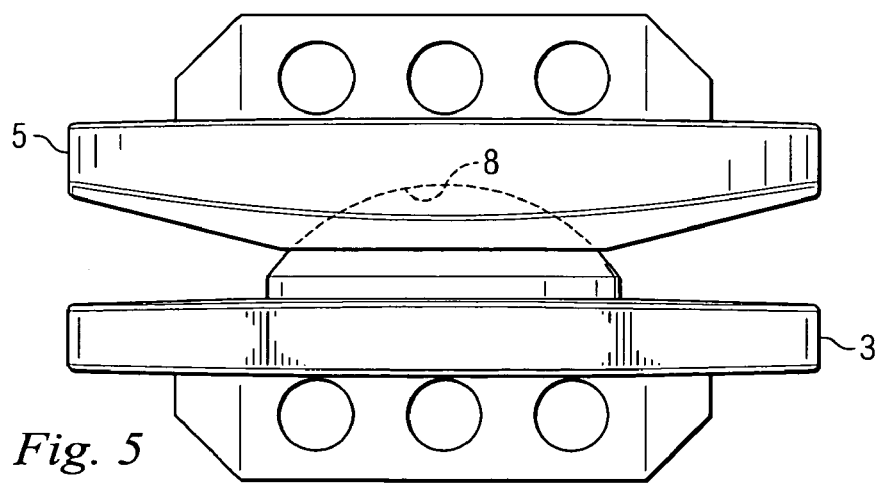
FIG. 5 is an elevation view of embodiments of inferior and superior bearings coupled together.
Figure 7:
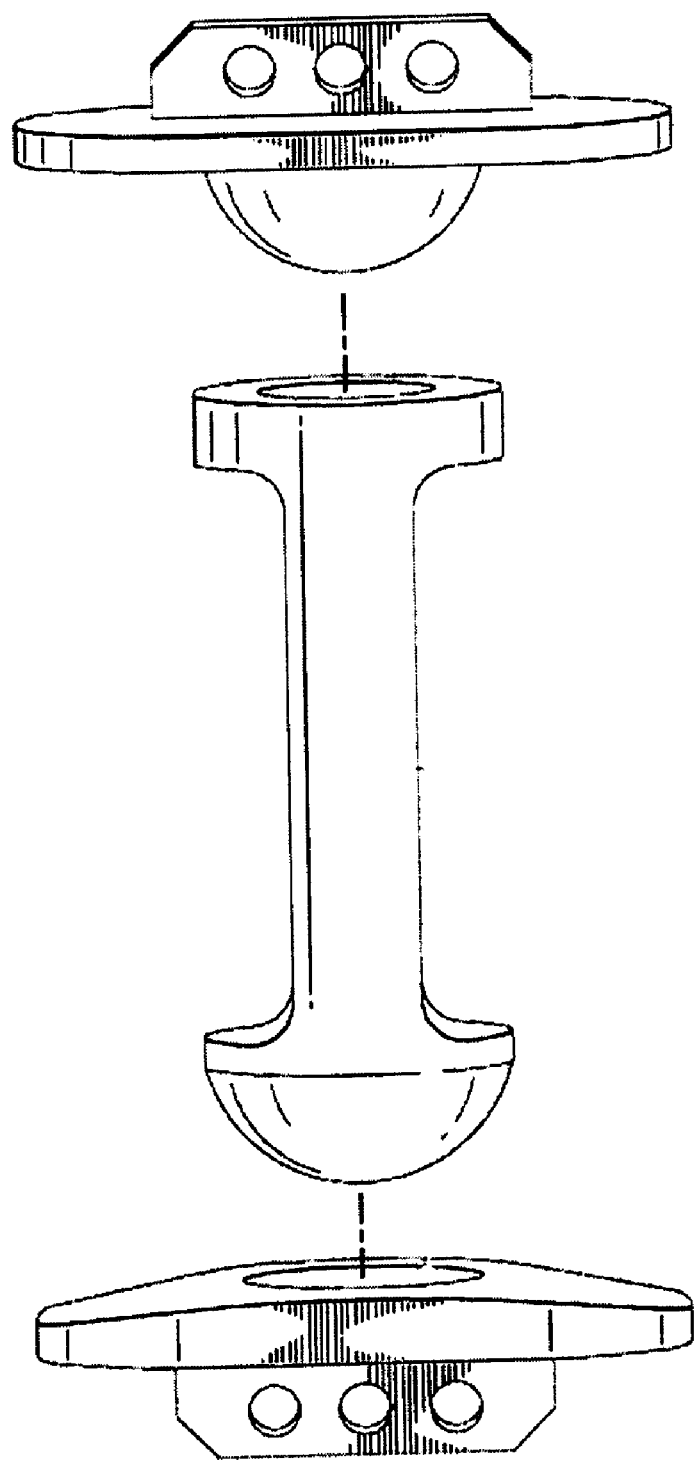
FIG. 7 is a an exploded view of an embodiment of an implantable corpectomy device showing a convex portion of the joint as a part of the superior bearing and a concave portion of the joint as a part of the support member, and showing a concave portion of the joint as a part of the inferior bearing and a convex portion of the joint as a part of the support member.

FIG. 1 illustrates an implantable corpectomy device 1 implanted between vertebrae of the spine. An inferior bearing 3 is implanted into an inferior vertebral body, and a superior bearing 5 is implanted into a superior vertebral body. In the construct illustrated, one vertebral body has been removed and replaced by the corpectomy device 1. In other embodiments, more than one vertebral body could be replaced by a corpectomy device of the invention, or in some circumstances, the inferior bearing 3 and the superior bearing 5 could be implanted adjacent to one another and interact in a vertebral disc space without the removal of a vertebra. FIG. 5 illustrates the inferior bearing 3 adjacent with the superior bearing 5.

Methods of implanting inferior and superior bearings as well as various configurations of bearings adapted for use from a number of surgical approaches are described in U.S. patent application Ser. No. 10/042,589, "Intervertebral Prosthetic Joint," filed Jan. 9, 2002; Ser. No. 10/620,529, "Intervertebral Prosthetic Joint," filed Jul. 16, 2003; 60/446,963, "Articular Disc Prosthesis and Method for Treating Spondylolisthesis," filed Feb. 12, 2003; Ser. No. 10/744,157, "Articular Disc Prosthesis and Method for Treating Spondylolisthesis," filed Feb. 6, 2004; Ser. No. 10/752,725, "Device For Fusing Two Bone Segments," filed Jan. 7, 2004; Ser. No. 10/752,724, "Instrument and Method for Milling a Path Into Bone," filed Jan. 7, 2004; Ser. No. 10/752,860, "Mobile Bearing Articulating Disc," filed Jan. 7, 2004; Ser. No. 10/773,494, "Articular Disc Prosthesis For Lateral Insertion," filed Feb. 6, 2004; Ser. No. 10/773,814, "Articular Disc Prosthesis For Transforaminal Insertion," filed Feb. 6, 2004; Ser. No. 10/773,815, "Method and Device for Correcting Spondylolisthesis from the Lateral Approach," filed Feb. 6, 2004; Ser. No. 10/774,078, "Instruments and Methods for Aligning Implants for Insertion," filed Feb. 6, 2004; Ser. No. 10/774,157, "Articular Disc Prosthesis for Anterior-Oblique Insertion," filed Feb. 6, 2004 all of which are incorporated by reference herein. Any of the relevant implants, methods, or surgical approaches described in the incorporated references are adaptable for use with components of the present invention and are within the scope of the invention described and claimed herein.

A support member 7 is shown in FIG. 1 slidably engaged between the inferior bearing 3 and the superior bearing 5. As illustrated, there are rotatable couplings between both inferior bearing 3 and support member 7, and the superior bearing 5 and the support member 7. The term slidably engaged includes all engagements or couplings that permit some degree of sliding. For example, longitudinal sliding or rotational sliding would be encompassed by the term. The term rotatable is intended to include any rotational movement between the coupled ends about any of the three axes of rotation. In addition to the embodiments illustrated, rotatable would, for example, describe substantially flat or angular surfaces bearing against one another that are able to rotate about an axis substantially perpendicular to the plane of their surfaces. Hinges or captured ball-in-socket couplings are additional examples of rotatable couplings.

The most significant spinal loads are typically compressive forces applied along the axis of the spine. The corpectomy device 1 illustrated in FIG. 1 will provide support for these typical compressive loads. A portion of the loads applied through the spine shown in FIG. 1 would be transferred along the longitudinal axis of the support member 7 and though inferior bearing 3 and superior bearing 5. Other portions of the load may be borne by a fixation device 10 or by any posterior spinal processes left intact.

Figures 2, 3:
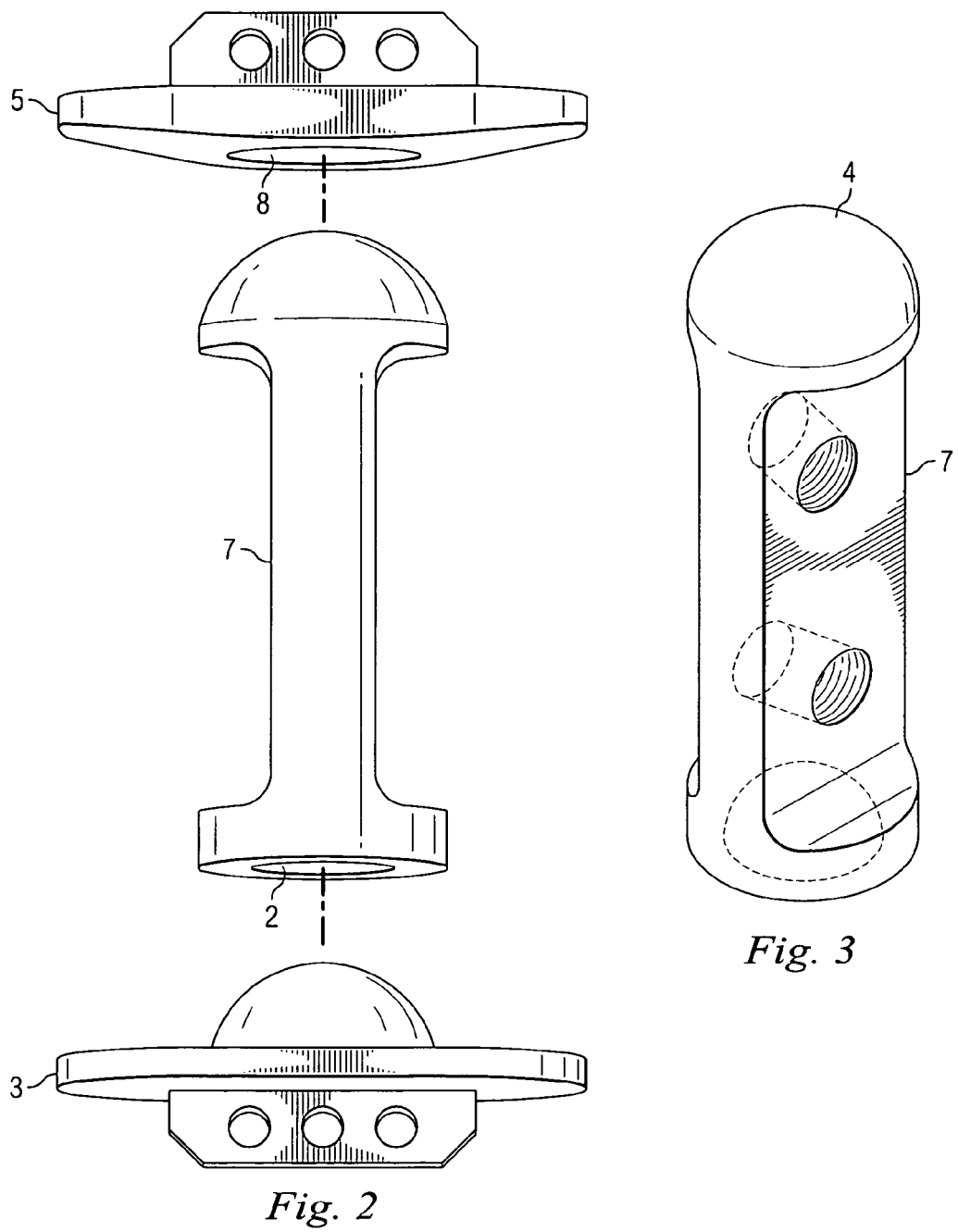
FIG. 2 is an exploded view of an embodiment of an implantable corpectomy device.
FIG. 3 is a perspective view of an embodiment of a support member.

A support member superior articular surface 4 is illustrated in FIG. 3. The surface 4 shown is a polished metallic surface designed to bear against a similar or complementary surface that interacts with the support member superior articular surface 4 in a manner that is tolerant of wear. Examples of wear tolerant surfaces include metallic alloys such as polished cobalt chrome or titanium, polymer materials such as ultra high molecular weight polyethylene, ceramic materials, and others. Any biocompatible material able to support the design loads also may be used with embodiments of the invention. The support member 7 may be made of one such material or of a combination of such materials that provides desired design characteristics. The support member superior articular surface 4 couples with a superior bearing articular surface 8 (FIG. 2). In the embodiment illustrated, the coupling between the superior bearing 5 and the support member 7 is a partial ball-in-socket joint. The superior bearing articular surface 8 is a concave surface, and the support member superior articular surface 4 is a convex surface. In other embodiments, the orientation or curvature of the respective surfaces may be altered to any configuration that is able to support the design loads while maintaining a degree of sliding or rotation between the components.

Figure 4:
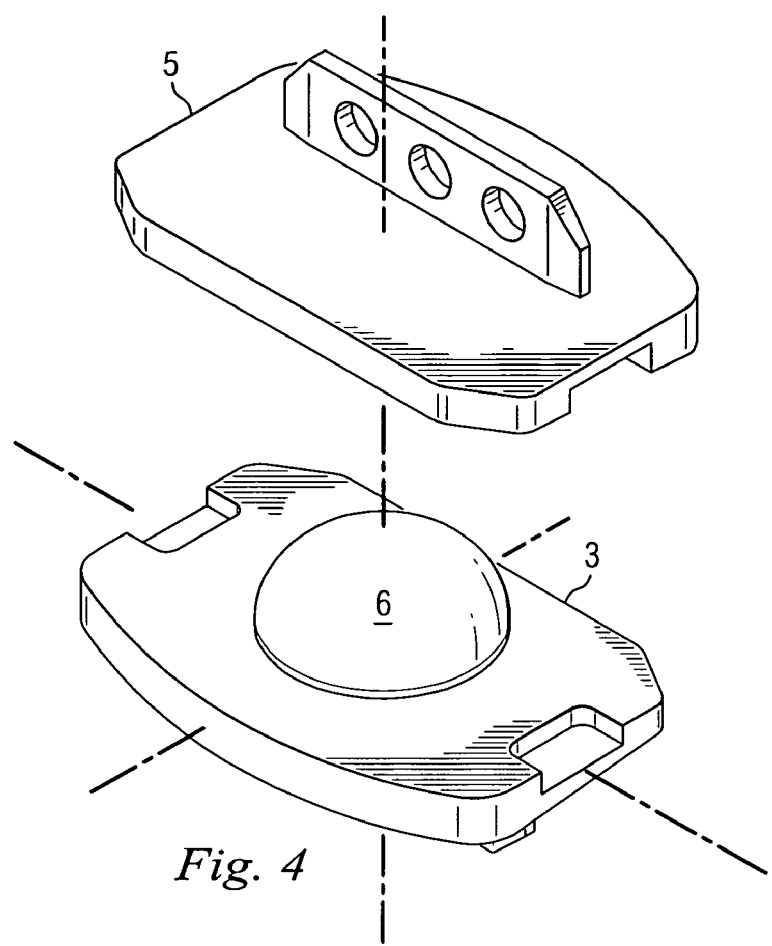
FIG. 4 is a perspective view of embodiments of inferior and superior bearings.

As illustrated in FIG. 2, the support member inferior articular surface 2 couples with inferior bearing articular surface 6 (FIG. 4). As shown, the coupling between the inferior bearing 3 and the support member 7 is a partial ball-in-socket joint.

The inferior bearing articular surface 6 is a convex surface, and the support member inferior articular surface 2 is a concave surface. In other embodiments, the orientation or curvature of the respective surfaces may be altered to any configuration that is able to support the design loads while maintaining a degree of sliding engagement between the components.

FIG. 1 shows a fixation device 10 attached to the inferior vertebral body with a first bone fixation element 16. The first bone fixation element 16 illustrated is a polyaxial bone screw with a mechanism for attaching and locking to a rod 14 from multiple angles. Those skilled in the art will appreciate that any element can be used instead of rod 14 for attaching bone fixation elements to one another, including, for example, flexible or arcuate rods, plates, polymeric materials, and the like. In other embodiments, the bone fixation element may be any device capable of attaching between a fixation device and a vertebral body. The fixation device 10 is coupled to the superior vertebral body with a second bone fixation element 18. A fastener 12 is illustrated coupling the fixation device 10 with the support member 7. As shown, one or more than one bone fixation elements 16, 18, can be used to attach the fixation device 10 to the inferior and superior vertebral bodies, including third and fourth bone fixation elements.

The illustrated fixation device 10 is a rod and screw system commonly used in the art to immobilize vertebrae, although any fixation device 10 can be used in the various embodiments of the invention. Fasteners 12 are multiaxial bolts adapted to engage with the support member 7. The threads applied to the bolt can be machine threads that engage with a tap in the support member 7. In other embodiments, the fasteners 12 may be screws or pins, and may engage with a relatively softer material from which the support member 7 is made or, alternatively, that is embedded in the support member 7. The fasteners 12 of some embodiments engage with a nut that is embedded in the support member 7. Such a nut (not shown) may be permitted to rotate about one or more axes relative to the support member 7. A multiaxial interface between the fixation device 10 and the support member 7 may be beneficial at least because it enables bolt or screw placement from a variety of angles. In some circumstances, approaches to the device may be limited by the anatomy or condition of a patient. The multiaxial embodiment shown and other such embodiments are valuable to enable approaches from a variety of angles.

The inferior bearing 3, the superior bearing 5, and the support member 7 combine to form a spinal implant system. In the spinal implant system, the inferior bearing 3 may be implanted in an inferior vertebral body, as shown in FIG. 1. The superior bearing 5 may be implanted in a superior vertebral body. The spinal implant system enables at least two general uses for the bearings 3, 5. In the use shown in FIG. 5, the inferior bearing 3 and the superior bearing 5 rotatably couple to each other to form a vertebral disc prosthesis. In this embodiment, a support member 7 and fixation device 10 may not be necessary. In the use shown in FIG. 1, the same or similar inferior bearing 3 and superior bearing 5 are rotatably coupled to respective ends of the support member 7 to form a corpectomy device.

The spinal implant system described is advantageous at least because it reduces the types of parts that must be stocked to provide systems that are useful to enable both vertebral disc replacement and vertebral body replacement (i.e. corpectomy). Embodiments of the invention allow for dual use of the bearings 3, 5. However, other embodiments do not require that an inferior bearing and a superior bearing be configured to both slidably couple with each other and with a support member.

The corpectomy device 1 illustrated in FIG. 1 may permit micro-motion at the interfaces of the support member 7 with the inferior bearing 3 and the superior bearing 5. Allowing controlled micro-motion may be advantageous because it permits an acceptable outlet for strain that does not affect the connection between the corpectomy device 1 and the anatomy. The corpectomy device 1 may not be capable of completely eliminating motion between the inferior vertebra and the superior vertebra. Therefore, if there is no controlled outlet for the strain generated by spinal forces, the strain will be expressed through deformations of components of the corpectomy device 1 and by stress on and potential loosening of the connections of the various components to the anatomy.

For example, the connections of the second fixation elements 18 to the superior vertebral body, the first fixation elements 16 to the inferior vertebral body, the inferior bearing 3 to the inferior vertebral body, and the superior bearing 5 to the superior vertebral body could be loosened in a device without articulating elements. However, allowing micro-motion at the interfaces of the support member 7 with the inferior bearing 3 and the superior bearing 5 assists in reducing the risk of such loosening. An embodiment of the invention therefore permits such micro-motion at these interfaces.

An additional embodiment of the invention includes a spinal implant and/or implantable corpectomy device that has an inferior bearing means for bearing against an inferior vertebral body and a superior bearing means for bearing against a superior vertebral body. The inferior bearing means and superior bearing means are capable of being implanted into the respective vertebral bodies. The spinal implant and/or implantable corpectomy device further may include a support means for providing support between the inferior bearing means and the superior bearing means, and optionally includes a fixation means. The fixation means may be a mechanism for coupling an inferior vertebral body and/or superior vertebral body to the support means, or a mechanism for coupling one or both inferior and superior bearing means.

The inferior bearing means, and the superior bearing means may be any device capable of bearing against a vertebral body, either by implanting directly into or onto the surface of the vertebral body, or by attachment using an external attachment mechanism such as adhesive, screw, bolt, or other attachment mechanism. The inferior bearing means and superior bearing means may be the same or similar to the inferior bearing 3 and superior bearing 5, as well as all known equivalents and equivalents later developed. The inferior and superior bearing means may be configured in any manner to permit bearing against an inferior and superior vertebral body. In one embodiment, the inferior bearing means is rotatably coupled to the superior bearing means. In this embodiment, a support means and a fixation means may or may not be employed.

The support means may be a supporting member capable of providing a support between the inferior bearing means and the superior bearing means. Any supporting member can be used, and the support means may be rotatably coupled to the inferior and superior bearing means. The support means may be the same or similar to the support member 7, as well as all known equivalents and equivalents later developed. The support means may include convex and concave shaped opposing ends to permit a rotatable coupling to the inferior and superior bearing means 3, 5.

The fixation means may be a device capable of fixing an inferior vertebral body and a superior vertebral body together, and may be used to couple the vertebral bodies to the support means, if utilized. Any vertebral fixation device now known or later discovered can be used as the fixation means. The fixation means can be the same or different from the fixation device 10, including its respective component parts, as well as all known equivalents and equivalents later developed.

Referring to FIG. 6a, in an alternative embodiment, socket and ball components 400, 402 each include a keel 404, 406, respectively, for engaging the vertebral bodies $V_1$, $V_2$ (FIG. 6b), respectively. A spacer device 410 is provided between the socket and ball components 400, 402 and includes a projection 412 corresponding to a recess 414 formed in the socket component 400. The spacer device 410 also includes a recess 416 corresponding to projection 418 extending from the ball component 402.

Referring to FIG. 6b, the socket and ball components 400, 402 are shown laterally engaged with the vertebral bodies $V_1$, $V_2$, respectively, and the spacer device 410 is shown engaged with the socket and ball components. It is understood that the socket and ball components 400, 402 may be inserted into the vertebral bodies $V_1$, $V_2$ from a variety of approaches other than the lateral approach, such as the anterior, transforaminal or anterior-oblique approaches. As is also illustrated, the spacer device 410 is positioned adjacent to a floating arch 420, the floating arch being the portion of vertebral body that remains after a vertebrectomy. The length of the spacer device 410 allows the spacer device to span between the socket and ball components 400, 402, thereby allowing articulating motion at both vertebral bodies $V_1$, $V_2$.

In some instances, it may be desirable to revise the arrangement of FIG. 6b in order to obtain a more stable interaction between the vertebral bodies $V_1$, $V_2$ and the prosthetic devices 400, 402, 410. Referring to FIG. 6c, in one embodiment, either of the socket and ball components 400, 402 can be secured to an adjacent vertebral bone, such as an arch 422, via a linkage 424. In another embodiment, and referring to FIG. 6d, the linkage 424 may also be secured to a posterior plate 428, which, is secured to another linkage 430. The linkage 430 can be configured to engage the spacer device 410. In either arrangement, motion is provided at only one of the vertebral bodies $V_1$, $V_2$, which provides for a more stable arrangement. It is understood that the linkages 424 and 430 and the posterior plate 428 can be formed of any bio-compatible material and that the various connections between the linkages and the posterior plate and between the linkages and the prosthetic devices can be accomplished by way of threaded, slotted or any other type of conventional connection means. Furthermore, it is understood that any number of fixation systems are contemplated for use with the embodiments of FIGS. 6c and 6d, such as ANTARES®, Z-PLATE™ and CD HORIZON® fixation systems sold by Medtronic Sofamor Danek, Inc.

Although not depicted, in another embodiment, stabilization can be achieved by removing the spacer device 410 and elongating either of the socket and ball components 400, 402 such that the socket and ball components engage one another in an articulating arrangement. Thus, motion would again only be provided at one of the vertebral bodies $V_1$, $V_2$, which would result in a relatively stable arrangement.

In other instances, it may be desirable to revise the arrangement of FIG. 6b in order to obtain a more mobile interaction between the vertebral bodies $V_1$, $V_2$ and the prosthetic devices 400, 402, 410. Although not depicted, it is contemplated that the spacer device 410 may be provided with a socket and ball arrangement to provide a third articulating segment between the vertebral bodies $V_1$, $V_2$.

Another embodiment of the invention is a method of implanting a corpectomy device. The method may include implanting an inferior bearing 3 into an inferior vertebra and implanting a superior bearing 5 into a superior vertebra. The bearings placed may be similar to the bearings illustrated in FIG. 5, or may be similar to any of the embodiments disclosed in the applications incorporated by reference herein. The bearings may be of any configuration that provides an interface for coupling with a vertebral body and may be constructed of any structurally capable biocompatible material.

In some methods of the invention, a support member, such as support member 7, is placed between the inferior bearing and the superior bearing. The support member may be rotatably coupled to the inferior bearing and rotatably coupled to the superior bearing. The order of placement of the bearings and the support member may vary among various embodiments of the invention.

A fixation device may be included with certain embodiments of the invention to provide additional stability to the corpectomy device. The fixation device may be coupled to the inferior vertebra with one or more bone fixation elements, and/or to the superior vertebra with one or more bone fixation elements. In some embodiments, the rigidity of the corpectomy device is increased by coupling the fixation device to the support member. Coupling the fixation device to the support member with a fastener may include the use of one or more multiaxial fasteners as are shown in the illustrated embodiments. Multiaxial fasteners may enable easier positioning of a fastener to align the fastener with a connection point in the support member. Once aligned, connection of the multiaxial fastener to the fixation device may be made. The illustrated multiaxial fastener has an engaging element that can be tightened to restrict multiaxial rotational movement of the fastener. Tightening of the engaging element provides additional rigidity to the corpectomy device.

In still a further embodiment, bearings such as inferior bearing 3 and superior bearing 5 may be implanted to achieve either a disc replacement or a corpectomy. A revision to repair or replace implanted devices sometimes becomes medically necessary. In such an embodiment, one of the inferior bearing or the superior bearing is removed. A replacement for the removed bearing is implanted. Because of the cooperating characteristics of the bearings and support members of the invention, a bearing originally implanted for use in a disc replacement may be employed as part of a corpectomy construct. Similarly, a bearing originally implanted as a part of a single level corpectomy may be employed as part of a two level corpectomy construct.

Various embodiments of the invention have been described in detail with reference to particularly preferred embodiments and figures. Those skilled in the art will appreciate that various modifications may be made to the invention without departing from the spirit and scope thereof.

What is claimed is:

1. An implantable corpectomy device comprising:
   an inferior bearing configured to be coupled with an inferior vertebral body;
   a support member extending along a first longitudinal axis and rotatably engaged with the inferior bearing, the support member having a thickness transverse to the first longitudinal axis, the thickness extending from a first outer surface to an opposite outer surface, the support member having first and second preformed apertures extending entirely through the thickness of the support member and sized and shaped for respectively receiving a first multiaxial fastener and a second multiaxial fastener, the first preformed aperture extending along a second longitudinal axis substantially transverse to the first longitudinal axis and the second preformed aperture extending along a third longitudinal axis substantially transverse to the first longitudinal axis, the third longitudinal axis extending at an oblique angle relative to the second longitudinal axis, wherein the support member is configured to transfer load along its longitudinal axis and into the inferior bearing;

a superior bearing configured to be coupled with a superior vertebral body and rotatably engaged with the support member, wherein the support member is configured to transfer load along its longitudinal axis and into the superior bearing; and a fixation device configured to be coupled with the inferior vertebral body through a first bone fixation element at one end of the fixation device, the fixation device configured to be coupled with the superior vertebral body through a second bone fixation element at an opposite end of the fixation device, and the fixation device configured to be coupled with the support member, wherein one of the engagement between the inferior bearing and the support member and the engagement between the superior bearing and the support member is at least a partial ball-in-socket joint; and the first and second multiaxial fasteners extending entirely through the first and second preformed apertures, respectively, from the first outer surface to a location beyond the opposite outer surface for securely coupling the fixation device and the support member to enable fastener placement from a variety of angles, the first and second multiaxial fasteners each having first and second portions, with the first portion being pivotable relative to the second portion.

2. The implantable corpectomy device of claim 1 wherein the engagement between the inferior bearing and the support member is at least a partial ball-in-socket joint.

3. The implantable corpectomy device of claim 2 wherein a convex portion of the joint is a part of the inferior bearing and a concave portion of the joint is a part of the support member.

4. The implantable corpectomy device of claim 2 wherein a concave portion of the joint is a part of the inferior bearing and a convex portion of the joint is a part of the support member.

5. The implantable corpectomy device of claim 1 wherein the engagement between the superior bearing and the support member is at least a partial ball-in-socket joint.

6. The implantable corpectomy device of claim 5 wherein a convex portion of the joint is a part of the superior bearing and a concave portion of the joint is a part of the support member.

7. The implantable corpectomy device of claim 5 wherein a concave portion of the joint is a part of the superior bearing and a convex portion of the joint is a part of the support member.

8. The implantable corpectomy device of claim 1 wherein the fixation device is a rod and screw system, the rod being sized and arranged to extend longitudinally beyond the bearings.

9. The implantable corpectomy device of claim 1 wherein at least one of the first and second multiaxial fasteners comprises at least one multiaxial bolt that is configured to extend between the fixation device and the support member at multiple angles.

10. The implantable corpectomy device of claim 1, wherein the fixation device comprises a first elongated rod and a second elongated rod, the first multiaxial fastener coupled to the first elongated rod and the second multiaxial fastener coupled to the second elongated rod.

11. An implantable corpectomy device comprising:
an inferior bearing means for bearing against an inferior vertebral body;
a superior bearing means for bearing against a superior vertebral body;
a support means for providing support between and rotatably coupled to the inferior bearing means and the superior bearing means, the support means extending along a first longitudinal axis and having a thickness transverse to the first longitudinal axis, the thickness extending from a first outer surface to an opposite outer surface, the support member having first and second preformed apertures extending entirely through the thickness of the support member and sized and shaped for respectively receiving a first multiaxial fastener and a second multiaxial fastener, the first preformed aperture extending along a second longitudinal axis substantially transverse to the first longitudinal axis and the second preformed aperture extending along a third longitudinal axis substantially transverse to the first longitudinal axis, the third longitudinal axis extending at an oblique angle relative to the second longitudinal axis;
a fixation means for coupling the superior vertebral body, the inferior vertebral body, and the support means while not coupling to the inferior and superior bearing means; and
the first and second multiaxial fasteners extending entirely through the first and second preformed apertures, respectively, from the first outer surface to a location beyond the opposite outer surface aperture for securely coupling the fixation means and the support means to enable fastener placement from a variety of angles, the first and second multiaxial fasteners each having first and second portions, with the first portion being pivotable relative to the second portion.

12. The implantable corpectomy device of claim 11 comprising a partial ball-in-socket joint rotatably coupling the inferior bearing and the support member.

13. The implantable corpectomy device of claim 12 wherein a convex portion of the joint is a part of the inferior bearing and a concave portion of the joint is a part of the support member.

14. The implantable corpectomy device of claim 11 comprising a partial ball-in-socket joint rotatably coupling the superior bearing and the support member.

15. The implantable corpectomy device of claim 14 wherein a convex portion of the joint is a part of the superior bearing and a concave portion of the joint is a part of the support member.

16. The implantable corpectomy device of claim 11 wherein the fixation means is a rod and screw system, the rod being sized and arranged to extend longitudinally beyond the bearings.

17. The implantable corpectomy device of claim 11 wherein at least one of the first and second multiaxial fasteners comprises at least one multiaxial bolt that is configured to extend between the fixation device and the support member at multiple angles.

18. A spinal implant system comprising:
an inferior bearing configured to be coupled with an inferior vertebral body, the inferior bearing having a first portion of a first rotatable coupling;
a support member extending along a first longitudinal axis and having a second portion of the first rotatable coupling configured to rotatably engage with the first portion, and the support member having a third portion of a second rotatable coupling disposed opposite said second portion, the support member having a thickness transverse to the first longitudinal axis, the thickness extending from a first outer surface to an opposite outer surface, the support member having first and second preformed apertures extending entirely through the thickness of the support member and sized and shaped for respectively receiving a first multiaxial bolt and a second multiaxial bolt, the first preformed aperture extending along a second longitudinal axis substantially transverse to the first longitudinal axis and the second preformed aperture extending along a third longitudinal axis substantially transverse to the first longitudinal axis, the third longitudinal axis extending at an oblique angle relative to the second longitudinal axis;

a superior bearing configured to be coupled with a superior vertebral body, the superior bearing having a fourth portion of the second rotatable coupling being configured to rotatably engage with the third portion of the second rotatable coupling; and a fixation device configured to couple to one or both of the inferior vertebral body and the superior vertebral body with one or more bone fixation elements, and the fixation device coupled to the support member with the first and second multiaxial bolts extending entirely through the first and second preformed apertures, respectively, from the first outer surface to a location beyond the opposite outer surface for securely coupling the fixation device and the support member at multiple angles, while not coupling to one or both respective inferior and superior bearings disposed between the support member and said one or both of the inferior vertebral body and the superior vertebral body.

19. The spinal implant system of claim 18 wherein one of the support member second and third portions is at least a partial ball-in-socket joint.

20. The spinal implant system of claim 19 wherein the support member second portion is substantially concave.

21. The spinal implant system of claim 19 wherein a concave portion of the first joint is a part of the inferior bearing and a convex portion of the first rotatable joint is a part of the support member.

22. The spinal implant system of claim 18 wherein the support member third portion is at least a partial ball-in-socket joint.

23. The spinal implant system of claim 22 wherein a convex portion of the second joint is a part of the superior bearing and a concave portion of the second joint is a part of the support member.

24. The spinal implant system of claim 22 wherein the support member third portion is substantially convex.

25. The spinal implant system of claim 18 wherein the fixation device is a rod and screw system, the rod being sized and arranged to extend longitudinally beyond the bearings.

26. The spinal implant system of claim 18 wherein the superior and inferior bearings each includes outwardly facing surfaces that are configured to contact the respective vertebral bodies and opposing inwardly facing surfaces, the support member being configured to engage with the superior and inferior bearings at a substantially central location on the inwardly facing surfaces.

27. An implantable corpectomy device comprising:
an inferior bearing configured to be coupled with an inferior vertebral body;
a support member extending along a first longitudinal axis and rotatably engaged with the inferior bearing, the support member having a thickness transverse to the first longitudinal axis, the thickness extending from a first outer surface to an opposite outer surface, the support member having first and second preformed apertures extending entirely through the thickness of the support member and sized and shaped for respectively receiving a first multiaxial fastener and a second multiaxial fastener, the first preformed aperture extending along a second longitudinal axis substantially transverse to the first longitudinal axis and the second preformed aperture extending along a third longitudinal axis substantially transverse to the first longitudinal axis, the third longitudinal axis extending at an oblique angle relative to the second longitudinal axis, wherein the support member is configured to transfer load along its longitudinal axis and into the inferior bearing;

a superior bearing configured to be coupled with a superior vertebral body and rotatably engaged with the support member, wherein the support member is configured to transfer load along its longitudinal axis and into the superior bearing;

a fixation device configured to be coupled with at least one of the inferior vertebral body and the superior vertebral body through a first bone fixation element at one end of the fixation device, and the fixation device configured to be coupled with the support member, while not coupling to the respective one of the superior and inferior bearing configured to be disposed between the support member and said at least one of the inferior vertebral body and the superior vertebral body; and the first and second multiaxial fasteners extending entirely through the first and second preformed apertures, respectively, from the first outer surface to a location beyond the opposite outer surface for securely coupling the fixation device and the support member to enable fastener placement from a variety of angles, the first and second multiaxial fasteners each having first and second portions, with the first portion being pivotable relative to the second portion.

28. The implantable corpectomy device of claim 27 wherein the rotatable engagement between the inferior bearing and the support member is at least a partial ball-in-socket joint.

29. The implantable corpectomy device of claim 28 wherein a convex portion of the joint is a part of the inferior bearing and a concave portion of the joint is a part of the support member.

30. The implantable corpectomy device of claim 28 wherein a concave portion of the joint is a part of the inferior bearing and a convex portion of the joint is a part of the support member.

31. The implantable corpectomy device of claim 27 wherein the rotatable engagement between the superior bearing and the support member is at least a partial ball-in-socket joint.

32. The implantable corpectomy device of claim 31 wherein a convex portion of the joint is a part of the superior bearing and a concave portion of the joint is a part of the support member.

33. The implantable corpectomy device of claim 27 wherein the fixation device is a rod and screw system, the rod being sized and arranged to extend longitudinally beyond the bearings.

34. The implantable corpectomy device of claim 27 wherein at least one of the first and second multiaxial fasteners comprises at least one multiaxial bolt that is configured to extend between the fixation device and the support member at multiple angles.

* * * * *